United States Patent [19]

Phillips et al.

[11] Patent Number: 5,442,104
[45] Date of Patent: Aug. 15, 1995

[54] INHIBITORS OF KYNURENINASE

[75] Inventors: Robert S. Phillips; Rajesh K. Dua, both of Athens, Ga.

[73] Assignee: University of Georgia Research Foundation, Inc., Athens, Ga.

[21] Appl. No.: 184,788

[22] Filed: Jan. 21, 1994

Related U.S. Application Data

[63] Continuation of Ser. No. 840,408, Feb. 24, 1992, abandoned, which is a continuation-in-part of Ser. No. 689,705, Apr. 18, 1991, Pat. No. 5,254,725.

[51] Int. Cl.$^6$ ............... C07C 317/10; C07C 317/14; C07C 317/28
[52] U.S. Cl. ..................... 562/430; 560/12; 560/13
[58] Field of Search ............ 562/430, 11, 444; 560/13, 39, 12

[56] References Cited

U.S. PATENT DOCUMENTS

| | | | |
|---|---|---|---|
| 4,293,569 | 10/1981 | Haugwitz et al. | 560/13 |
| 4,332,813 | 6/1982 | Firestone | 562/430 |
| 4,609,673 | 9/1986 | Eggerer et al. | 560/13 |
| 4,730,008 | 3/1988 | Skidmore et al. | 560/13 |

OTHER PUBLICATIONS

Goodman et al., *J. Org. Chem.*, 23, pp. 1251–1257 (1958).
Damgolou et al. (1971) The Biochem. J. 123:379–384.
Tarzia et al. (1988) Synthesis 7:514–517.
Crescenzi et al. (1990) Gazzetta Chimica Italiana 120.
Flynn et al. (1984) Tetra. Lett. 25(25):2655–2658.
McCapra et al. (1976) J. Chem. Soc., Chem. Comm. 5:153–154.
Gilchrist et al. (1979) J. Chem. Soc., Chem. Comm. 5:1089–1090.
Abstract entitled "S–Aryl–L–Cysteine Sulfone: A New Class of Mechanism Based Inhibitors of Kynureninase", ACS Meeting 6 (1992).
Phillips and Dua (1991) J. Amer. Chem. Soc. 113:7385–7388.
Phillips and Dua (1991) Abstracts of Papers of the American Chemical Society vol. 201, APR, P. 283–ORGN, "Stereochemistry and Mechanism of Aldol Reactions Catalyzed by Kynureninase".
Crescenzi et al. (1990), Gazzetta Chimica Italiana, 120.

*Primary Examiner*—Joseé G. Dees
*Assistant Examiner*—Barbara S. Frazier
*Attorney, Agent, or Firm*—Greenlee and Winner

[57] ABSTRACT

The present invention provides inhibitors of kynureninase having the formula

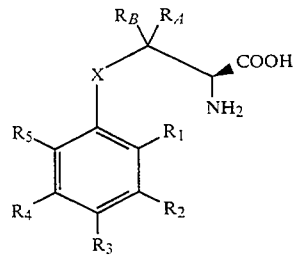

where X is CHOH, S, SO$_2$, SO, SONH$_2$, PO$_2$H or PONH$_2$, R$_a$ and R$_b$, independently of one another are H, a halogen, CF$_3$ or a small alkyl group having one to three carbon atoms; R$_1$ is H, NH$_2$, NR$_6$RT, NO$_2$, halogen, CF$_3$ or a small alkyl group having from one to three carbon atoms, wherein: R$_6$ and R$_7$, independently of one another, are H, a formyl group or a small alkyl group having from one to three carbon atoms with the exception that only one of R$_6$ or R$_7$ can be a formyl group; R$_2$ is OH, H, halogen, CF$_3$ or a small alkyl group having from one to three carbon atoms; and R$_3$, R$_4$ and R$_5$, independently of one another, are H, halogen, CF$_3$, NO$_2$, NH$_2$, or small alkyl group having from one to three carbon atoms. In particular, compounds of this formula in which X is CHOH, S or SO$_2$ are provided. In compounds of this formula in which X is CHOH, those having the ($\alpha$S,$\gamma$S) configuration or the ($\alpha$R,$\gamma$R) configuration when R$_A$ or R$_B$ is a hydrogen, are more potent inhibitors of kynureninase. Inhibitors of mammalian kynureninase are of particular use in therapy for certain neurological disorders.

12 Claims, No Drawings

INHIBITORS OF KYNURENINASE

This invention was made through a grant from the National Institutes of Health. The United States Government has certain rights in this invention.

This is a continuation of application Ser. No. 07/840,408, filed on Feb. 24, 1992, now abandoned. Which application is a continuation-in-part of U.S. Ser. No. 07/689,705, filed Apr. 18, 1991, now U.S. Pat. No. 5,254,725.

BACKGROUND OF THE INVENTION

Kynureninases are a group of pyridoxal-5'-phosphate dependent enzymes which catalyze the hydrolytic cleavage of aryl-substituted α-amino-γ-keto acids, particularly L-kynurenine or 3-hydroxy-L-kynurenine to give L-alanine and anthranilic acid or 3-hydroxyanthranilic acid, respectively (see: K. Soda and K. Tanizawa (1979)Advances Enzym. 49:1–40). Kynureninase is involved in the microbial catabolism of L-tryptophan via the aromatic pathway. In plants and animals, a kynureninase is required in tryptophan catabolism and for NAD biosynthesis via quinolinic acid. Quinolinic acid is a relatively toxic metabolite which has been implicated in the etiology of neurological disorders, including epilepsy and Huntington's chorea (R. Schwarcz et al. (1988) Proc. Natl. Acad. Sci. USA 85:4079; M. F. Beal et al. (1986) Nature 321:168–171; S. Mazzari et al. (1986) Brain Research 380:309–316; H. Baran and R. Schwarcz (1990) J. Neurochem. 55:738–744). Inhibitors of kynureninase are thus important targets for treatment of such neurological disorders.

L-kynurenine (which can also be designated α,2-diamino-γoxobenzenebutanoic acid) is the preferred substrate of bacterial kynureninase, which is exemplified by that of *Pseudomonas fluorescens* (O. Hayaishi and R. Y. Stanier (1952) J. Biol. Chem. 195:735–740). The kynureninase of tryptophan metabolism in plants and animals has a somewhat different substrate specificity with 3-hydroxy-L-kynurenine (which can be designated α,2-diamino-3-hydroxy-γ-oxo-benzenebutanoic acid) being the preferred substrate (Soda and Tanizawa (1979) supra).

The mechanism of kynureninases has been the subject of considerable interest due to the unique nature of this pyridoxal-5'-phosphate dependent reaction. Mechanisms based on redox reactions ((J. B. Longenecker and E. E. Snell (1955) J. Biol. Chem. 213:229–235) or transamination (C. E. Dalgleish et al. (1951) Nature 168:20–22) have been proposed. More recently mechanisms involving either a nucleophilic mechanism with an "acyl-enzyme" intermediate (C. Walsh (1979) "Enzymatic Reaction Mechanisms" W. H. Freeman and Co., San Francisco, p. 821; M. Akhtar et al. (1984) "The Chemistry of Enzyme Action" New Comprehensive Biochemistry, Vol. 6 (M. I. Page, ed.) Elsevier, N.Y., p.821) or a general base-catalyzed mechanism (K. Tanizawa and K. Soda (1979) J. Biochem. (Tokyo) 86:1199–1209) have been proposed.

In addition to the physiological reaction, kynureninase has been shown to catalyze an aldol-type condensation of benzaldehyde with incipient L-alanine formed from L-kynurenine to give α-amino-γ-hydroxy-γ-phenylbutanoic acid (G. S. Bild and J. C. Morris (1984) Arch. Biochem. Biophys. 235:41–47). The stereochemistry of the product at the γ-position was not determined, although the authors suggested that only a single isomer was formed.

J. L. Stevens (1985) J. Biol. Chem 260:7945–7950 reports that rat liver kynureninase displays cysteine conjugate β-lyase activity. This enzyme activity is associated with cleavage of S-cysteine conjugates of certain xenobiotics to give pyruvate, ammonia and a thiol, for example, cleavage of S-2-(benzothiazolyl)-L-cysteine to give 2-mercaptobenzothiazole, pyruvate and ammonia.

Several reports concerning the relative reactivities of kynurenine analogs with bacterial kynureninase or rat liver kynureninase are summarized in Soda and Tanizawa (1979) supra. Tanizawa and Soda (1979) supra reported that a number of ring substituted L-kynurenines, namely: 3-hydroxy-, 5-hydroxy-, 5-methyl-, 4-fluoro-, and 5-fluoro-L-kynurenine were substrates of kynureninase of *P. fluorescens*. These authors also reported that dihydrokynurenine (called γ-(o-aminophenyl)-L-homoserine therein) was a substrate for that kynureninase, yielding o-aminobenzaldehyde and L-alanine. The $K_m$ of dihydrokynurenine was reported to be 67 μM compared to a $K_m$ of 35 μM for L-kynurenine and 200 μM for 3-hydroxy-L-kynurenine. N'-formyl-L-kynurenine and β-benzoyl-L-alanine were likewise reported to be substrates (with $K_m$=2.2 mM and 0.16 mM, respectively) for the bacterial kynureninase. Tanizawa and Soda measured relative reactivity as relative amounts of L-alanine formed.

O. Hayaishi (1955) in "A Symposium on Amino Acid Metabolism" (W. D. McElroy and H. B. Glass, eds.) Johns Hopkins Press, Baltimore pp. 914–929 reported that 3-hydroxy- and 5-hydroxy-L-kynurenine, β-benzoyl-L-alanine and β-(o-hydroxybenzoyl)-L-alanine were substrates for the bacterial enzyme, but that N'-formyl-L-kynurenine was not a substrate. O. Hayaishi measured relative reactivities by determining the amount of substrate hydrolyzed.

Tanizawa and Soda (1979) supra reported that S-benzoyl-L-cysteine, L-asparagine and D-kynurenine were not substrates of kynureninase, while O. Hayaishi (1955) supra reported that β-(p-aminobenzoyl)-L-alanine, β-(o-nitrobenzoyl)-L-alanine, β-(m-hydroxybenzoyl)-L-alanine, 3-methoxy-L-kynurenine, β-benzoylpropanoic acid, andβ-(o-aminobenzoyl)propanoic acid do not react with bacterial kynureninase. Kynureninase is reported to act only on L-amino acids (M. Moriguchi et al. (1973) Biochemistry 12:2969–2974).

O. Wiss and H. Fuchs (1950) Experientia 6:472 (see: Soda and Tanizawa (1979) supra) reported that 3-hydroxy-L-kynurenine, L-kynurenine, β-benzoyl-L-alanine, γ-phenyl-L-homoserine, γ-methyl-L-homoserine, 2-aminolevulinic acid and α-amino-γ-hydroxypentanoic acid reacted with rat liver kynureninase to produce alanine, while β-(o-nitrobenzoyl)-L-alanine did not.

G. M. Kishore (1984) J. Biol. Chem. 259:10669–10674 has reported that certain β-substituted amino acids are mechanism-based inactivators of bacterial kynureninase. Several β-substituted amino acids including β-chloro-L-alanine, O-acetyl-L-serine, L-serine 0-sulfate, S-(o-nitrophenyl)-L-cysteine and β-cyano-L-alanine inactivated kynureninase. These β-substituted amino acids react with kynureninase to give pyruvate and ammonia. However, a portion of the turnovers of the enzyme lead to formation of an inactive enzyme complex. L-S-(o-nitrophenyl)-L-cysteine was described as the "most efficient suicide substrate at low concentrations" with a $K_i$ of 0.1 mM.

Bacterial kynureninase is also strongly inhibited by o-aminobenzaldehyde ($K_i=6.5$ μM, non-competitive inhibition). Several other aromatics having "a carboxyl group on the benzene ring and an amino group at the ortho-position" including o-aminoacetophenone, anthranilic acid o-nitrobenzaldehyde and benzaldehyde were described as inhibitors (Tanizawa and Soda (1979) supra). It was suggested that inhibition relates to binding of the formyl group to the portion of the enzyme that serves as a binding site for the γ-carboxyl of kynurenine. Anthranilate and 3-hydroxanthranilate, the products of the kynureninase reaction, were also reported to inhibit the enzyme (Takeuchi et al. (1980) J. Biochem. (Tokyo) 88:987-994).

J. P. Whitten et al. (1989) Tetrahedron Letts. 30:3649-3652 reported the synthesis of 2,2-difluoro-α-benzoyl alanine (α-amino-β,β-difluoro-γ-oxobenzene butanoic acid) which is said to be a "potential new inhibitor of kynureninase." Fluoroketone-containing peptides are described as capable of forming stable hydrates or hemiketals which are "thought to inhibit" proteolytic enzymes as analogs of a tetrahedral transition state. The difluoro compound is described as a competitive inhibitor of kynureninase, but no details of this inhibition are given in the reference.

The present work is based on a reexamination of the mechanism of kynureninase catalysis, in particular, through an investigation of the stereospecificity of the retroaldol reaction catalyzed by the enzyme. During the course of this work, the reactivity of dihydrokynurenine with kynureninase was found to be significantly different than had previously been reported. The result of these mechanism and reactivity studies was the identification of a class of potent kynureninase inhibitors. The present invention provides kynureninase inhibitors which were designed to be "transition-state analogue" inhibitors.

SUMMARY OF THE INVENTION

It is an object of the present invention to provide means and compositions for inhibition of kynureninase. The inhibitors of this invention are amino acid derivatives of the formula:

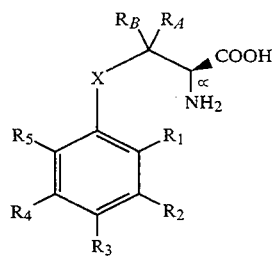

wherein the stereochemical configuration at the α carbon is indicated (the same configuration as in L-kynurenine) where X is CHOH, S, $SO_2$, SO, SONH, $PO_2H$, or $PONH_2$, wherein $R_a$ and $R_b$, independently of one another are H, halogen, $CF_3$ or a small alkyl group having one to three carbon atoms; $R_1$ is H, halogen, $NH_2$, $NR_6R_7$, $NO_2$, $CF_3$, or a small alkyl having from one to three carbon atoms; with $R_6$ and $R_7$, independently of one another, being H, $CH_3$ or COH wherein only one of $R_6$ or $R_7$ can be COH; $R_2$ is OH, H, halogen, $CF_3$, or a small alkyl having from one to three carbon atoms; and $R_3$, $R_4$ and $R_5$, independently of one another, are H, OH, halogen, $CF_3$, $NO_2$, $NH_2$, or a small alkyl group having from one to three carbon atoms.

X is preferably CHOH, S or $SO_2$ with $SO_2$ being generally more preferred than S.

It is preferred that the halogen is fluorine, that $R_2$ is H or OH, that $R_1$ is H or $NH_2$, and that $R_A$, $R_B$, $R_4$ and $R_5$ are H or fluorine. It is preferred that $R_3$ is H, $NH_2$, $NO_2$ or fluorine, with H or fluorine more preferred. It is more preferred that $R_1$ is $NH_2$ and $R_A$, $R_B$, $R_3$, $R_4$ and $R_5$ are H.

For inhibition of bacterial kynureninase, it is preferred that $R_2$ is H. For inhibition of plant and animal kynureninase, it is preferred that $R_2$ is OH.

It is a specific object of the present invention to provide kynureninase inhibitors which are derivatives of α-amino-γ-hydroxy-γ-hydroxybenzene butanoic acids of the formula:

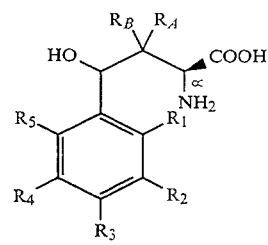

wherein the stereochemical configuration at the α carbon is as indicated (the same configuration as L-kynurenine), wherein $R_a$ and $R_b$, independently of one another are H, halogen, $CF_3$ or a small alkyl group having one to three carbon atoms; $R_1$ is H, halogen, $NH_2$, $NR_6R_7$, $NO_2$, $CF_3$ or a small alkyl group having from one to three carbon atoms, with $R_6$ and $R_7$, independently of one another, being H, $CH_3$ or COH, wherein only one of $R_6$ or $R_7$ can be COH; $R_2$ is OH, H, halogen, $CF_3$, or a small alkyl group having from one to three carbon atoms; and $R_3$, $R_4$ and $R_5$, independently of one another, are H, OH, halogen, $CF_3$, $NO_2$, $NH_2$, or a small alkyl group having from one to three carbon atoms. It is preferred that the halogen is fluorine, that $R_2$ is H or OH that $R_1$ is $NH_2$ or H and that $R_A$, $R_B$, $R_3$, $R_4$ and $R_5$ are H or fluorine. It is more preferred that $R_1$ is $NH_2$ and that $R_A$, $R_B$, $R_3$, $R_4$ and $R_5$ are H.

For inhibition of bacterial kynureninase it is preferred that $R_2$ is H. For inhibition of plant and animal kynureninase it is preferred that $R_2$ is OH.

It is a more specific object of this invention to provide kynureninase inhibitors which are α-amino-γ-hydroxy-γ-aryl butanoic acids having the structure:

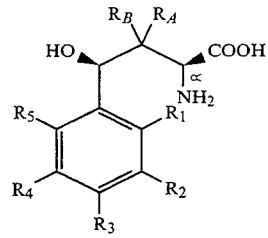

wherein the stereochemical configuration at the α and γ carbons is as indicated (the configuration at the α carbon being the same as in L-kynurenine) and wherein $R_{1-7}$, $R_A$ and $R_B$ are as defined above for formulas I and II. For inhibition of bacterial kynureninase it is preferred that $R_2$ is H. For inhibition of plant and animal kynureninase it is preferred that $R_2$ is OH.

It is a second specific object of this invention to provide S-aryl derivatives of L-cysteine which are inhibitors of kynureninase having the formula:

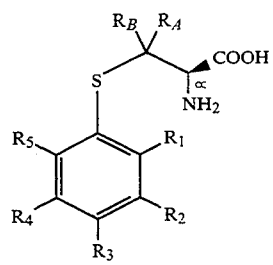

IV where the stereochemical configuration at the α-carbon is as indicated (the same as in L-kynurenine) where $R_{1-7}$, $R_A$ and $R_B$ are as defined for formulas I, II and III.

It is a further specific object of this invention to provide S-aryl-L-cysteine sulfones which are inhibitors of kynureninase having the formula:

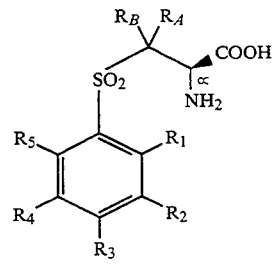

V where the stereochemical configuration at the α-carbon is as indicated (the same as in L-kynurenine) and $R_{1-7}$, $R_A$ and $R_B$ are as defined for formulas I-IV.

Salts of the compounds of formulas I-V are considered functional equivalents thereof with respect to inhibition of kynureninase. In particular, pharmaceutically acceptable salts of the compounds of formulas I-V are useful for the methods of the present invention and are useful in any therapeutic treatment of animals based on the inhibitory action of the compounds of formulas I-V.

Inhibitors of the present invention include, among others, ring fluorinated dihydrokynurenines: (αS,γS)- or (αS, γR)-α,2-diamino-γ-hydroxy-4-fluorobenzenebutanoicacid, (αS,γS)- or (αS,γR)-α,2-diamino-γ-hydroxy-4-fluorobenzenebutanoic acid; ring hydroxylated dihydrokynurenines: (αS,γS)- or (αS,γR)-α,2-diamino-γ,5-dihydroxybenzenebutanoic acid; ring methylated dihydrokynurenines (αS,γS)- or (αS,γR)-α,2-diamino-γ-hydroxy- 5-methylbenzenebutanoic acid, or ring-substituted (αS,γS)- or (αS,γR)-α-amino-γ,2-dihydroxybenzenebutanoic acid.

Inhibitors of kynureninase also include dihydroxynurenines: (αS,γS)-α,2-diamino-γ-hydroxybenzenebutanoic acid and (αS,γR)-α,2-diamino-γ-hydroxybenzenebutanoic acid; 3-hydroxydihydrokynurenines: (αS,γS)-α,2-diamino-γ,3-dihydroxybenzenebutanoic acid and (αS,γR)-α,2-diamino-γ,3-dihydroxylbenzenebutanoic acid and dihydrodesaminokynurenines: (αS,γS)-α-amino-γ-hydroxybenzenebutanoic acid and (αS,γR)-α-amino-γ-hydroxybenzenebutanoic acid. Dihydrokynurenine and dihydrodesaminokynurenine ( see Soda and Tanizawa (1979) Supra p. 32, Table VIII) were previously reported to be substrates for certain kynureninases. Alternate substrates will act as competitive inhibitors toward the "natural" enzyme substrate. Dihydrokynurenine (Tanizawa and Soda (1979) supra) was reported to react readily with bacterial kynureninase with a reactivity about 65% that of L-kynurenine. The dihydrokynurenine employed in that reference was indicated to be a mixture of the (αS,γS) and (αS,γR) dihydrokynurenine diastereomers. It was not disclosed therein and the data given therein do not suggest that one of the diastereomers (αS,γS) is not a substrate for the kynureninase but acts as a competitive inhibitor of the enzyme for reaction of its natural substrates.

It is a further object of this invention to provide a method of inhibiting kynureninase in vitro and/or in vivo which comprises the step of contacting the enzyme with an inhibitory amount of one or more of the compounds of formulas I-V or salts, particularly pharmaceutically acceptable salts, thereof. It is well understood in the art that a precursor prodrug may be converted in vivo to a therapeutically active drug. Any such prodrug precursors of the compounds of formulas I-V are encompassed by this invention.

Therapeutic applications of the methods of the present invention relate particularly to inhibition of animal kynureninases, particularly those of mammals. Inhibitors in which $R_1$ is $NH_2$ and $R_2$ is OH are preferred for such therapeutic applications.

Compounds of the present invention that are preferred for therapeutic applications of the methods of the present invention are those that have minimal toxic or irritant effect toward the target of the therapy. If the inhibitor reacts with kynureninase, it is important that the product of that reaction be substantially nontoxic.

Kynureninases from different sources have different substrate preferences. For example, the preferred substrate of mammalian kynureninase is 3-hydroxy-L-kynurenine rather than L-kynurenine. In general, for a particular kynureninase, a preferred inhibitor of formula I-V will possess the phenyl ring substitutions of a preferred substrate of that kynureninase.

DETAILED DESCRIPTION OF THE INVENTION

Kynureninases catalyze the hydrolysis of aryl-substituted γ-keto-α-amino acids. Kynureninase has been identified and isolated from certain bacteria, fungi, yeasts as well as from mammalian sources. Kynureninases from different sources have been reported to have different substrate specificities. L-kynurenine is the preferred "natural" substrate of bacterial kynureninase. In contrast for mammalian, yeast and fungal kynureninases, 3-hydroxy-L-kynurenine is the preferred "natural" substrate. This preference for 3-hydroxy-L-kynurenine, as assessed by relative substrate $K_m$'s, is characteristic of animal and plant kynureninases. The relative affinities of kynureninases for substrates other than L-kynurenine and 3-hydroxy-L-kynurenine can also depend on the source of the enzyme. Animal and plant kynureninases are sometimes called 3-hydroxykynureninases. The term kynureninase as used herein includes both bacterial, plant and animal kynureninases. Bacterial kynureninases are exemplified by the enzyme isolated from Pseudomonas fluorescens. Mammalian kynureninase is exemplified by the enzyme isolated from mammalian liver, in particular rat liver. A bacterial kynureninase will generally display substrate specificity like that of the P. fluorescens kynureninase. Mammalian kynureninase will generally display substrate specificity like that of rat liver kynureninase. Kynureninases, from all sources, catalyze the same types of reactions and so the mechanisms of the reactions they catalyze should be the same. Differences in affinities for substrates is believed to be associated with differences in the substrate binding site.

The present invention provides inhibitors of kynureninase. Some of these inhibitors are substrates of the enzyme, some are not substrates. Many of the inhibitors of this invention are competitive inhibitors of the enzyme for their natural substrates L-kynurenine and 3-hydroxy-L-kynurenine.

Inhibition, as used herein, refers to inhibition of the hydrolysis of L-kynurenine and 3-hydroxy-L-kynurenine. Competitive inhibition and noncompetitive inhibition can be assessed by in vitro methods well-known in the art. Preferred inhibitors of a particular kynureninase are those having a $K_i$ less than or equal to the $K_m$ of the preferred substrate either L-kynurenine or 3-hydroxy-L-kynurenine for that kynureninase. In general for competitive inhibitors, it is preferred that the inhibitor have an affinity equal to or greater than that of the preferred substrate for the enzyme. The level of inhibition that is achieved is dependent on the concentration of inhibitor in the vicinity of the enzyme. In general, the higher the affinity of the enzyme for the inhibitor, the more potent an inhibitor is. For applications of the methods of inhibition of kynureninase, particularly therapeutic applications, it is generally preferred to employ high affinity (low $K_i$) inhibitors to minimize the amount of inhibitor that must be administered.

Kynureninases are known to catalyze other reactions, for example, cysteine conjugate β-lyase activity. Inhibition of kynureninases can also be, at least qualitatively, assessed employing in vitro assays for such alternate kynureninase activities.

The aldol reaction of L-kynurenine and benzaldehyde catalyzed by kynureninase was found to proceed to give predominantly (80%) the (αS, γR) diastereomer of α-amino-γ-hydroxybenzenebutanoic acid.

The stereospecificity of the aldol reaction, as well as the results of Bild and Morris, Arch. Biochem. Biophys. (1984) 235:41–47, supports a general base mechanism for kynureninase, as shown in Scheme I. The stereospecificity for cleavage of the (4R)-isomer is likely a reflection of favorable orientation for the active site general base to initiate the retro-aldol cleavage by proton abstraction (Scheme IA).

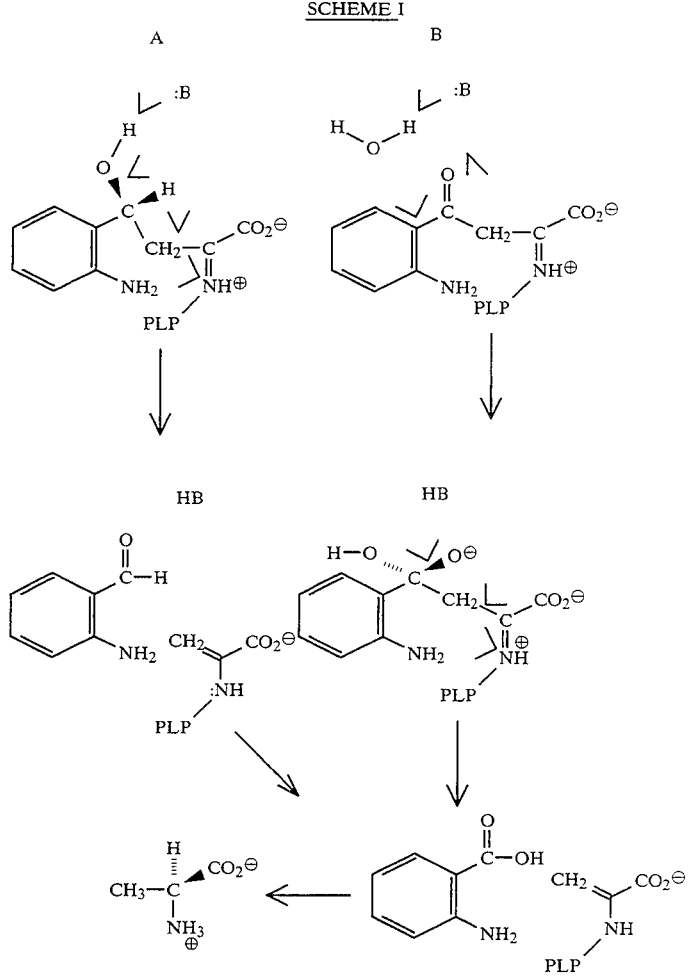

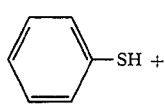

Scheme II

-continued
Scheme II

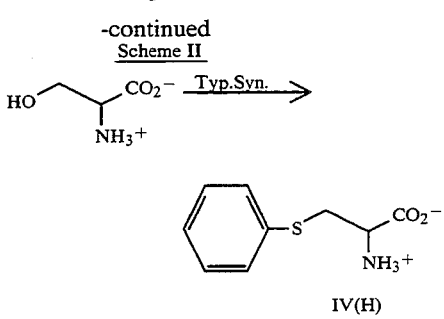

Scheme III

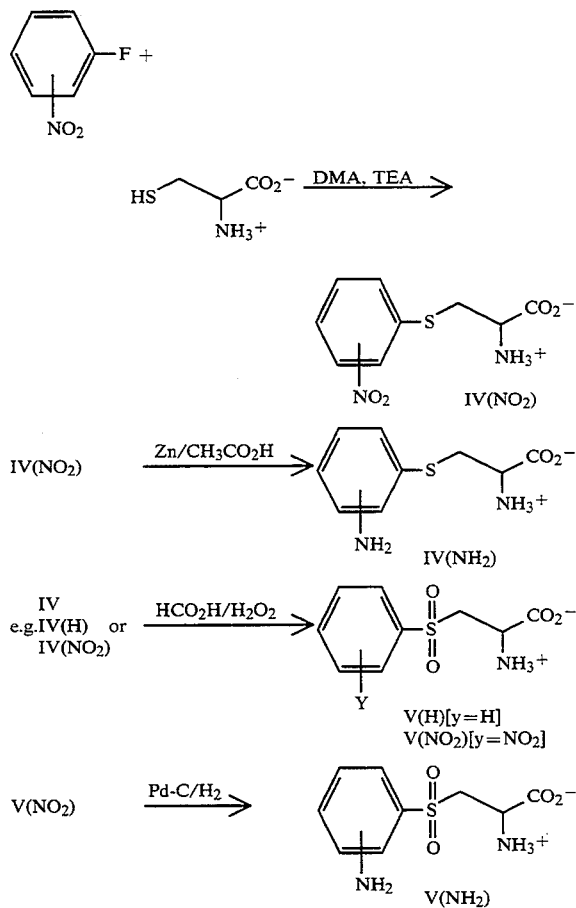

The basic group involved is probably the carboxylate that Kishore (1984) supra reported is modified by suicide substrate inhibitors. Although Kishore proposed that this carboxylate is responsible for α-proton abstraction, stereochemical studies by Palcic et al., J. Biol. Chem. (1985) 260:5248–5251, found that a α-proton of kynurenine is scrambled between the α and β-positions of the L-alanine product, and thus the proton abstraction at the α-C is probably due to a polyprotic base, most likely a lysine ε-amino group. In the hydrolysis of L-kynurenine, the second general base would be required to assist in hydration of the ketone, by abstraction of a proton from a water molecule (Scheme IB). The observed stereochemistry of the aldol-reactions suggests that the water attacks on the reface of the carbonyl group, giving the (S)-gem-diolate anion. Subsequent rapid collapse of this tetrahedral intermediate is likely and would generate the enzyme-bound enamine of PLP-L-alanine and anthranilic acid (Scheme IB). In the case of the (4S)-isomer, the carbinol group would mimic this gem-diol tetrahedral intermediate, but is not oriented in a position favorable for the retro-aldol reaction to occur. Thus, this compound is a "transition-state analogue," and would be expected to bind to kynureninase very tightly.

As an extension of these mechanistic studies, the reactivities of dihydrokynurenine diastereomers were examined. (αS,γ)-Dihydrokynurenine (αS,γ)-α,2-diamino-γ-hydroxybenzenebutanoic acid) was found to be a slow substrate for the retro-aldol cleavage reaction catalyzed by kynureninase, while the analogous (αS,γS) diastereomer was unreactive. When these compounds were included in reaction mixtures of enzyme and L-kynurenine, the reaction was strongly inhibited. Analysis of the kinetic data in the presence of various concentrations of the dihydrokynurenines demonstrated that they act as competitive inhibitors with respect to kynurenine, and the data indicate that (αS,γS)-dihydrokynurenine binds more tightly than does L-kynurenine. This increased affinity of (αS,γS)-dihydrokynurenine is characteristic of mechanism-based, or "transition-state analogue" inhibitors.

The design of the kynureninase inhibitors of the present invention was based on the results of the inhibition studies on the diastereomers of dihydrokynurenine in combination with what is known of substrate specificity of kynureninases.

Although not wishing to be bound by any specific theory, it is believed that the inhibitors of the present invention represent "transition-state analogue" inhibitors of kynureninase in view of the newly proposed mechanism of Scheme I. Based on this proposed mechanism α-amino-γ-hydroxybenzenebutanoic acids having electron withdrawing groups, including but not limited to, $CF_3$, halogen, $NO_2$, CN etc. appropriately substituted on the benzene ring to stabilize the proposed "transition state" will act as inhibitors of the kynureninase.

The kynureninase inhibitors of the present invention can be prepared as exemplified for the preparation of the dihydrokynurenine diastereomers by selective reduction of the keto group of an appropriate γ-keto-amino acid or by other methods well known in the art. Kynurenines, including various ring-substituted kynurenines, can be prepared by ozonolysis of tryptophans. Alternatively, kynurenine analogs with desired ring substitution can be prepared enzymatically from appropriate tryptophans as described in Tanizawa and Soda (1979) supra and O. Hayaishi (1953) in Biochemical Preparations (E. E. Snell, ed.) Vol. 3, John Wiley & Sons, Inc., New York, pp. 108–111. The γ-keto amino acid, β-benzoyl-DL-alanine can be prepared in several ways (for example, C. E. Dalgleish (1952) J. Chem. Soc. 137–141 and F. M. Veronese et al. (1969) Z. Naturforsch. 24:294–300) including amination of β-benzoylacrylate (Tanizawa and Soda (1979) supra). β-Benzoyl alanines having various desired ring substitution can be prepared using analogous methods starting with appropriately substituted starting materials. Hayaishi (1955) supra and Wiss and Fuchs (1950) supra also provide sources of γ-keto amino acids useful for preparation of the compounds of the present invention. β-Benzoyl alanines can be selectively reduced by means known to the art to produce the inhibitors of the present invention.

Similarly, β-substituted γ-keto amino acids can serve as precursors to the β-(or 2-)substituted γ-hydroxy amino acids of the present invention. Whitten et al. (1990) supra, provides a synthesis of 2,2-difluoro-2-benzoyl alanine which can be selectively reduced to give α-amino-γ,γ-difluoro-γ-hydroxybenzenebutanoic acid. Analogous methods can be employed to prepare β-substituted, phenyl-ring substituted γ-hydroxybenzenebutanoic acids of the present invention.

As will be appreciated by those in the art, reduction of a chiral nonracemic γ-keto amino acid, preferably an L-amino acid will generally result in a mixture of diastereomers. Techniques are available and well known in the art for the separation of diastereomers (HPLC, preparative TLC, etc.).

S-(nitrophenyl)-L-cysteines (IV (NO2)), were synthesized by nucleophilic aromatic substitution of fluoronitrobenzenes with L-cysteine in DMF in the presence of triethylamine (Phillips et al. (1989) Enzyme Microb. Techno. 11:80–83). The unsubstituted S-phenyl-L-cysteine (IV (H)) was synthesized enzymatically following a procedure by Soda et al. (1983) 47(12):2861 (Scheme II). This method involves incubating thiophenol with L-serine in the presence of tryptophan synthase at 37.5° C. for 48 hrs. Reduction of S-(nitrophenyl)-L-cysteines was accomplished by stirring with Zn dust and acetic acid. The oxidation of thioethers to sulfones was achieved by using a procedure described by Goodman et al. (1958) J. Org. Chem 23:1251, with slight modifications. This method produced good results when the aryl cysteines were treated with a mixture of formic acid (98%) and hydrogen peroxide (30%). However, when 88% formic acid was used for this reaction a slightly impure product was obtained and the yields were also lower. The ease of formation of the sulfone depends on the position of nitro group on the ring. When a nitro group is present at the ortho position the completion of reaction took 48 hours or more, whereas, when there is no nitro group on the ring or when the nitro group is at the 4-position, the reaction is complete in 12 hours. Reduction of the nitro sulfones was performed by catalytic hydrogenation using acetic acid or formic acid as solvent (Scheme III).

Sulfoxide derivatives (I where X=SO) of the present invention can be prepared from known and readily available starting materials by means well-known to the art, for example, by oxidation of corresponding thioethers as described in Example 7 in the presence of a limiting amount of hydrogen peroxide.

Sulfoxamide derivatives of this invention can also be prepared from known and readily available starting materials by means well-known to the art.

Phosphinate and phosphinamide derivatives (I where X =PO2H or PONH2) can be prepared from known and readily available starting materials by means well-known in the art, for example, by the Arbuzov reaction (Arbuzov. (1964) Pur Appl. Chem. 9:307–335) or routine modifications thereof.

The results of competitive inhibition of certain thioether and sulfone compounds are shown in Table 1. Among all the compounds tested, the unsubstituted S-phenyl-L-cysteine was found to be a very weak inhibitor, with $K_i$ value of 0.7 mM, however, its oxidized analog, S-phenyl-L-cysteine sulfone, showed a 180 fold decrease in $K_i$ value to 3.9 μM. Similarly, substitution of an ortho-amino group in the S-(2-aminophenyl)-L-cysteine showed a 318 fold decrease in $K_i$ to 2.2 μM. The compound which combined both of these structural features, S-(2-aminophenyl)-L-cysteine sulfone turned out to be the most potent inhibitor of kynureninase, with $K_i$ of about 70 nM. A similar, but less significant improvement in the activity of the compounds were observed by sulfone formation in the cases of 2-nitro,4-nitro and 4-amino compounds. The results discussed above on the potent inhibition by dihydrokynurenines indicate that the kynureninase reaction proceeds via a gem-diol intermediate. The results of Table 1 indicate that the oxygens on the sulfur mimic the gem-diol tetrahedral transition state in the reaction of L-kynurenine with kynureninase. Therefore, these compounds are additional examples of transition state analogs. The presence of amine group and its position on the aromatic ring plays an important role in the activity of the compound. When the amine group is moved from the 2-position to the 4-position of the ring, the activity of the compound drops 50-fold in case of cysteines and 120-fold in case of the respective sulfones. This regiospecificity is expected, since the 2-aminophenyl-L-cysteines are closer structural analogues of kynurenine. The presence of the nitro group on the ring decreases the activity of all the compounds by several fold, possibly due to unfavorable steric interactions.

As has been described herein, one of the pair of diastereomers in cases in which diastereomers can exist, will be a preferred kynureninase inhibitor. It will be appreciated, however, that inhibition can be obtained by use of a mixture of the diastereomers. In order to obtain maximal inhibition for the amount of inhibitor employed, it will be preferable to maximize the amount of the more inhibitory diastereomer in the mixture.

TABLE 1

Competitive Inhibition of Kynureninase.

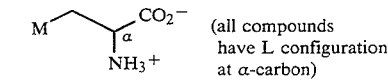

(all compounds have L configuration at α-carbon)

| M | $K_i(\mu M)$ |
|---|---|
| 1. 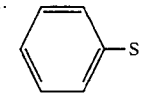 | 700 |
| 2. 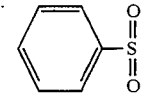 | 3.9 |
| 3. 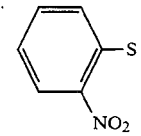 | 100 |
| 4. 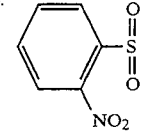 | 23 |
| 5. 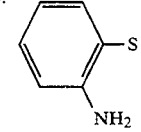 | 2.5 |

TABLE 1-continued

Competitive Inhibition of Kynureninase.

M-C(α)(NH3+)(CO2−) (all compounds have L configuration at α-carbon)

| M | $K_i(\mu M)$ |
|---|---|
| 6. 2-aminophenyl-SO2- | 0.07[1] |
| 7. 4-nitrophenyl-S- | — |
| 8. 4-nitrophenyl-SO2- | 12 |
| 9. 4-aminophenyl-S- | 140 |
| 10. 4-aminophenyl-SO2- | 8.5 |

[1]This value is an upper limit. $K_i$ here is approximately the same order of magnitude as the concentration of enzyme in the assay, so that the steady-state approximation may not apply.

EXAMPLES

Example 1

Investigation of the Mechanism of Kynureninase-catalyzed adol-reactions.

Bacterial kynureninase was prepared from cells of *Pseudomonas fluorescens* (ATCC 11250, for example) essentially as described by Hayaishi and Stanier (1952) J. Biol. Chem. 195:735–740. Cells were grown on a minimal medium containing 0.1% L-tryptophan as the sole carbon and nitrogen source.

From 100 l of medium, grown for 18 h at 30° C., 230 g of wet cell paste was obtained. The cells were suspended in 1 l of 0.01M potassium phosphate, pH 7.0, and disrupted by 2 passages through a Manton-Gaulin homogenizer. After centrifugation of the cell extract for 1 h at 10000 g, the enzyme was partially purified by ion-exchange chromatography on DEAE-cellulose and ammonium sulfate precipitation. The preparation used in the results of Table 1 exhibited a specific activity of 0.2 μmol min⁻¹ mg⁻¹.

L-kynurenine and benzaldehyde (in excess) were incubated with kynureninase under the conditions described by Bild and Morris (1984) Arch. Biochem. Biophys. 235:41–47, which is incorporated by reference herein. The product of this reaction was purified by preparative HPLC and identified as α-amino-γ-hydroxybenzenebutanoic acid. This product was produced in quantitative yield based on L-kynurenine.

The α-amino-γ-hydroxybenzenebutanoic acid produced in the kynureninase reaction exhibited a negative CD (circular dichroism) extremum at 260 nm, with vibronic splitting characteristic of a chirally substituted benzoyl alcohol chromophore. Based on a comparison of the CD spectra of the product with those of (R)- and (S)-mandelic acids, the predominant chiral product was determined to have the same absolute configuration as (S)-mandelic acid and thus to have the (γR)-configuration. (The terms R and S are employed as is conventional according to the Cahn-Ingold-Prelog rules.) NMR analysis (300 MHz, $^1$H) of the product demonstrates that it is an 80:20 mixture of (αS,γR):(αS,γS) diastereomers of α-amino-γ-hydroxybenzene butanoic acid.

Example 2

Reactivity of Dihydrokynurenine with Kynureninase.

L-kynurenine (from commercial sources) was reduced with NaBH4 in H2O to give dihydrokynurenine [α,2-diamino-γ-hydroxybenzenebutanoic acid]. The progress of reaction was monitored by the disappearance of the 360 nm UV absorption band of L-kynurenine. The reduction resulted in a 60:40 mixture of diastereomers. The diastereomers were separated by preparative HPLC on a 20×250 mm C18 column (Rainin, Dynamax) eluting with 0.1% acetic acid (5 ml/min). The first peak to elute from the HPLC column was identified by $^1$H NMR analysis to be the (αS,γS)-diastereomer. The second peak to elute was identified by $^1$H NMR analysis to be the (αS,γR)-diastereomer.

The CD spectra of the separated dihydrokynurenine diastereomers were consistent with this identification.

The reactivity of the two dihydrokynurenines with kynureninase in 0.1M potassium phosphate buffer, pH 8.0, at 25° was examined. Reaction was followed by the appearance of o-aminobenzaldehyde, as determined spectrophotometrically by the increase in absorbance at 360 nm (See Tanizawa and Soda (1979) Biochem. (Tokyo) 86:1199–1209, which is incorporated by reference herein).

The (αS,γR)-dihydrokynurenine diastereomer reacted slowly with kynureninase to produce o-aminobenzaldehyde. No significant reaction of the (αS,γS)-diastereomer was detected. Tanizawa and Soda (1979) supra had reported that dihydrokynurenine reacted with kynureninase with a Vmax of about 65% that of L-kynurenine. In contrast, the present work indicates that only the (αS,γR)-diastereomer of dihydrokynurenine reacts, only at about 5% of the rate of L-kynurenine. Under the conditions employed and with the bacterial kynureninase prepared as described in Example 1, $K_m$ of the reaction of L-kynurenine was determined to be 25 μM. This value is similar to the $K_m$ of 35 μM for L-kynurenine obtained by Tanizawa and Soda.

Example 3

Inhibition of Kynureninase by Dihydrokynurenine.

Inhibition of kynureninase by dihydrokynurenine was measured by including the potential inhibitor in the enzyme assay mixture (see Example 1 and Tanzawa and Soda (1979) supra) and determining the apparent Km for L-kynurenine (the preferred substrate of bacterial kynurenine) in the absence and presence of the potential inhibitor. $K_i$ values were then calculated using the standard equation:

$$(K_m)_{app} = K_m(1 + [I]/K_i)$$

where [I] is the molar concentration of inhibitor and $K_m = 25$ μM.

Inhibition of kynureninase by the (αS,γR)- and (αS,γS)-diastereomers of dihydrokynurenine was examined and $K_i$'s were determined. Both compounds strongly inhibited the reaction of kynureninase with L-kynurenine. The $K_i$ value for the (αS, γS)-diastereomer was lower than for the (αS,γR)-diastereomer. Both compounds were found to be competitive inhibitors of kynureninase.

Inhibition of mammalian kynureninase can be measured using several different assays for enzyme activity. Rat liver kynureninase is obtained from homogenization of rat liver, followed by precipitation with $(NH_4)_2SO_4$, as described by Steven, J. L., J. Biol. Chem. (1985) 260:7945–7950, which is incorporated by reference herein. The activity of rat liver kynureninase was assessed by measurement of the cysteine conjugate β-lyase activity, as described by Steven (supra), with S-(2-benzothiazolyl)cysteine, a nonphysiological chromophoric substrate. Inhibition of kynureninase by the dihydrokynurenine diastereomers was assessed with respect to reaction with that substrate.

Both the (αS,γR) and (αS,γS) diastereomers of dihydrokynurenine were found to inhibit the reaction of rat liver kynureninase. The (αS,γS) diastereomer was found to be the stronger competitive inhibitor with $K_i$ under the assay conditions of about 690 μM.

Example 4

Synthesis of S-(phenyl)-L-cysteines (IV (H)).

A mixture containing 1.23 ml (12 mM) of thiophenol, 0.525 g (5 mM) of L-serine, 10 μM of potassium phosphate buffer, pH 7.8, 0.13 mg (20 nM) of pyridoxal-5'-posphate and 5 mg of tryptophan synthase in a total volume of 25 ml was stirred at 37.5° C. After 48 hours the reaction mixture was cooled, the thick white precipitate was filtered and washed with water and ethanol to give 0.31 g of white crystals of S-(phenyl)-L-cysteine.

Tryptophan synthase was purified from cells of *E. coli* CB149 with plasmid pSTB7 containing the trpA and trpB genes from *Salmonella typhimurium*, as described by Miles et al. (1989) J. Biol. Chem. 264:6280.

Example 5

Synthesis of S-(nitrophenyl)-L-cysteines ($IV(NO_2)$).

To a flask containing 5 g of L-cysteine, 4.47 g of fluoronitrobenzene and 20 ml of DMF was added 7.84 ml of triethylamine. After stirring at room temperature for 3–4 hours, the contents of the flask solidifed into a thick yellow cake. This solid was mixed with 15–20 ml of water and filtered to give crude S-nitrophenyl-L-cysteine. Recrystalization from hot water gave lemon yellow crystals of the product.

Example 6

Synthesis of S-(aminophenyl)-L-cysteines ($IV(NH_2)$).

0.4 g of the S-nitrophenyl compound was dissolved in 50 mL of acetic acid, 2.0 g of zinc dust was added, and the mixture stirred at room temperature overnight. After completion of the reaction, the solid was filtered on celite and the filtrate was concentrated in vacuo to give an oil. This oil was triturated with water and methanol to give an off white solid of the reduced compound.

Example 7

Synthesis of S-phenyl and S-nitrophenyl-L-cysteine sulfones (V(H) and $V(NO_2)$).

0.65 g of S-phenyl or S-nitrophenyl compound was dissolved in 20 ml of 98% formic acid and 4 ml of 30% hydrogen peroxide, and the mixture stirred at room temperature for 12–48 hours, depending on the compound as discussed above. After completion of the reaction, the solvent was carefully evaporated in vacuo at 25°–30° C. to give a white solid of the desired product.

Example 8

Synthesis of S-(aminophenyl)-L-cysteine sulfones ($V(NH_2)$).

0.4 g of nitrophenyl sulfone was dissolved in 50 ml of formic acid, 0.045 g of 10% Pd—C was added, and the mixture hydrogenated for 30 minutes. The charcoal was removed by filtration on celite and the filtrate was concentrated in vacuo to give a light tan oil, which upon trituration with methanol gave a light tan solid of the aminophenyl sulfone.

Example 9

Competitive Inhibition of Kynureninase by Compounds (IV and V).

Kynureninase activity was measured at 25° C. by following the decrease in absorbance at 360 nm ($\epsilon = -4500$ $M^{-1}$ $cm^{-1}$). A typical assay mixture contained 0.4 mM L-kynurenine in 0.04M potassium phosphate, pH 7.8, containing 40 μM pyridoxal-5'-phosphate, at 25° C. The reactions of S-aryl cysteines and S-aryl cysteine sulfones with kynureninase were performed using a spectrophotometric coupled assay with lactate dehydrogenase and NADH, by monitoring a decrease in absorbance due to pyruvate formation. A typical assay mixture contained 30 μl lactate dehydrogenase solution (2 mg/ml), 0.1 mM NADH, 40 μM pyridoxal-5'-phosphate, 0.04M Tris.HCl buffer, pH 7.8, with varying concentrations of the compounds. The competitive inhibition of these compounds was measured by variation of L-kynurenine concentrations at several fixed values of the inhibitor. $K_m$ and $V_{max}$ values were calculated by fitting of initial rate data to the Michaelis-Menten equation with ENZFITTER (Elsevier) on a Z-286 personal computer. KI values were determined from the equation:

$$v = V_{max}[S]/(K_m(1+[I]/K_i)+[S])$$

Results for certain compounds of formulas IV–IX are given in Table 1.

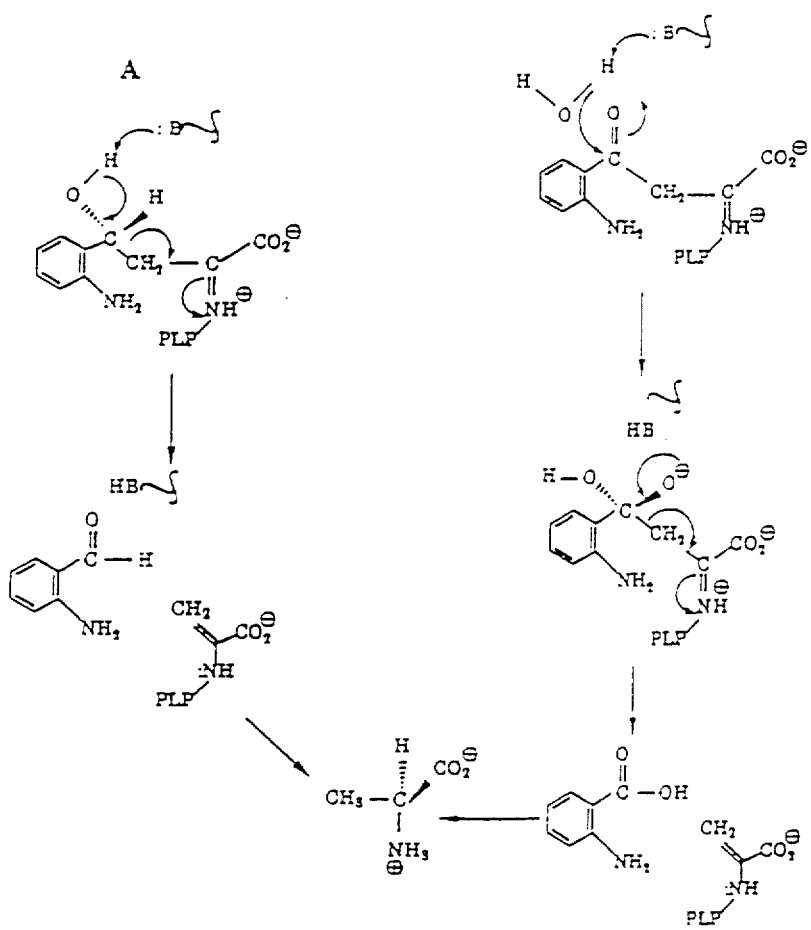

We claim:

1. A kynureninase inhibitor selected from the group consisting of compounds having the formula:

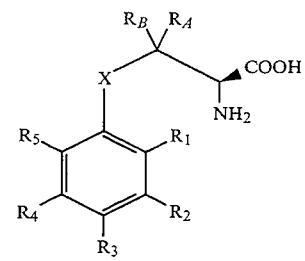

wherein

X is $SO_2$, SO, $SONH_2$;

$R_a$ and $R_b$, independently of one another are H, a halogen, $CF_3$ or a small alkyl group having one to three carbon atoms;

$R_1$ is H, $NH_2$, $NR_6R_7$, $NO_2$, halogen, $CF_3$ or a small alkyl group having from one to three carbon atoms, wherein:

$R_6$ and $R_7$, independently of one another, are H, a formyl group or a small alkyl group having from one to three carbon atoms with the exception that only one of $R_6$ or $R_7$ can be a formyl group;

$R_2$ is OH, H, halogen, $CF_3$ or a small alkyl group having from one to three carbon atoms; and $R_3$, $R_4$ and $R_5$, independently of one another, are H, halogen, $CF_3$, $NO_2$, $NH_2$ or small alkyl group having from one to three carbon atoms.

except that where X is $SO_2$ and each of $R_A$, $R_B$, $R_2$, $R_3$, $R_4$ and $R_5$ is H, $R_1$ cannot be H or a small alkyl group having from one to three carbon atoms; where X is $SO_2$ and each of $R_A$, $R_B$, $R_1$, $R_3$, $R_4$ and $R_5$ is H, $R_2$ cannot be $CF_3$ or a small alkyl group having from one to three carbon atoms; where X is $SO_2$ and each of $R_A$, $R_B$, $R_1$, $R_2$, $R_4$ and $R_5$ is H, $R_3$ cannot be $NO_2$, $CF_3$, a halogen, or a small alkyl group having from one to three carbon atoms; where X is SO and each of $R_A$, $R_B$, $R_1$, $R_3$, $R_4$ and $R_5$ are H, $R_3$ cannot be H or a small alkyl group having from one to three carbon atoms, and when X=SO, and $R_2$, $R_4$, $R_5$ are all H, $R_3$ cannot be a halogen, $NO_2$ or a small alkyl group having from one to three carbons.

2. The inhibitor of claim 1 wherein:

$R_A$ and $R_B$, independently of one another are H or F;

$R_1$ is $HN_2$, H or F;

$R_2$ is OH, H, or F; and $R_3$, $R_4$ and $R_5$, independently of one another, are H or F.

3. The inhibitor of claim 2 wherein $R_1$ is $NH_2$.

4. The inhibitor of claim 3 wherein $R_2$ is H.

5. The inhibitor of claim 2 wherein:

$R_A$, $R_B$, $R_3$, $R_4$ and $R_5$ are H;

$R_1$ is $NH_2$ or H; and $R_2$ is OH or H.

6. The inhibitor of claim 5 wherein $R_1$ is $NH_2$.

7. The inhibitor of claim 6 wherein $R_2$ is H.

8. The inhibitor of claim 6 wherein $R_2$ is OH.

9. The inhibitor of claim 1 in which X is $SO_2$.

10. The inhibitor of claim 9 in which $R_3$ is $NO_2$.

11. The inhibitor of claim 9 in which $R_1$ is $NH_2$ and $R_{2-5}$, $R_A$ and $R_B$ are all H.

12. A kynureninase inhibitor having the formula:

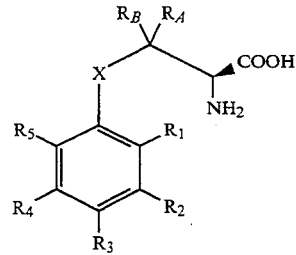

wherein X is SO or $SO_2$; wherein $R_1$ is $NH_2$; $R_2$ is OH, and $R_A$, $R_B$, $R_3$, $R_4$ and $R_5$, independently of one another, are H or F.

* * * * *

UNITED STATES PATENT AND TRADEMARK OFFICE
CERTIFICATE OF CORRECTION

PATENT NO. : 5,442,104
DATED : August 15, 1995
INVENTOR(S) : Robert S. Phillips, et al It is certified that error appears in the above-indentified patent and that said Letters Patent is hereby corrected as shown below:

In the Abstract, sixth line of text "$NR_6RT$," should read -- $NR_6R_7$,--.

At column 11, line 6, "α-amino-γ,γ-difluoro-γ-hydroxybenzenebutanoic" should read --α-amino-ß,ß-difluoro-γ-hydroxybenzenebutanoic--.

At column 8, please replace Scheme I as printed with the corrected Scheme I presented herewith.

Signed and Sealed this

Thirtieth Day of January, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,442,104
DATED : August 15, 1995
INVENTOR(S) : Robert S. Phillips; Rajesh K. Dua It is certified that error appears in the above-indentified patent and that said Letters Patent is hereby corrected as shown below:

At column 8, please replace Scheme I as printed with the corrected Scheme I presented herewith.